United States Patent
Ray et al.

(10) Patent No.: US 10,485,471 B2
(45) Date of Patent: Nov. 26, 2019

(54) SYSTEM AND METHOD FOR IDENTIFYING ICTAL STATES IN A PATIENT

(71) Applicant: The Trustees of Dartmouth College, Hanover, NH (US)

(72) Inventors: Laura Ray, Hanover, NH (US); Harrison King Saturley-Hall, Hanover, NH (US); Jim Lever, Lebanon, NH (US); Susan Taylor, Lebanon, NH (US); Erik Kobylarz, Lyme, NH (US); Seyed Mahdi Basiri Azad, Hanover, NH (US); Dvij Bajpai, Hanover, NH (US); Rebecca Butler, Hanover, NH (US); Latika Sridhar, Hanover, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 0 days.

(21) Appl. No.: 15/400,789

(22) Filed: Jan. 6, 2017

(65) Prior Publication Data

US 2017/0196497 A1 Jul. 13, 2017

Related U.S. Application Data

(60) Provisional application No. 62/276,203, filed on Jan. 7, 2016.

(51) Int. Cl.
*A61B 5/00* (2006.01)
*G06F 19/00* (2018.01)
(Continued)

(52) U.S. Cl.
CPC ............ *A61B 5/4094* (2013.01); *A61B 3/113* (2013.01); *A61B 5/0024* (2013.01);
(Continued)

(58) Field of Classification Search
CPC ... A61B 5/0002; A61B 5/002; A61B 5/02055; A61B 5/0402
See application file for complete search history.

(56) References Cited

U.S. PATENT DOCUMENTS 8,641,646 B2* 2/2014 Colborn ............... A61B 5/0245
600/595
2004/0158119 A1 8/2004 Osorio et al.
(Continued)

FOREIGN PATENT DOCUMENTS

| WO | 2004/03487 A2 | 4/2004 |
| WO | 2004/034880 A2 | 4/2004 |
| WO | 2013/185775 A1 | 12/2013 |

OTHER PUBLICATIONS

Boser et al. (1992) "A training algorithm for optimal margin classifiers," In; The Proceedings of the fifth annual workshop on Computational learning theory—COLT '92. pp. 144-152.
(Continued)

*Primary Examiner* — Lynsey C Eiseman
*Assistant Examiner* — Amanda L Steinberg
(74) *Attorney, Agent, or Firm* — Lathrop Gage LLP (57) ABSTRACT

A system and method for identifying ictal states in a patient, the system including a plurality of sensors for sensing different non-electroencephalographic signals from the patient, and a processing unit. The processing unit has a processor and memory with instructions for classifying data from the plurality of sensors to determine probability of the patient being ictal, when the probability is high asking the patient if the patient is in an ictal state, reporting to a caregivers if the patient is ictal, and updating the classifier based upon sensor data, probability, and the response. The method includes sensing, using a plurality of non-electro-encephalographic sensors, determining, using a classifier trained using a training dataset, probability of the patient
(Continued)

being in an ictal state, and if probability is high, asking the patient if the patient is in ictal state, logging the occurrence of an ictal state, and updating the classifier.

10 Claims, 8 Drawing Sheets

(51) Int. Cl.

| | | |
|---|---|---|
| *A61B 3/113* | (2006.01) | |
| *A61B 5/0205* | (2006.01) | |
| *A61B 5/0402* | (2006.01) | |
| *A61B 5/0488* | (2006.01) | |
| *A61B 7/04* | (2006.01) | |
| *A61B 5/11* | (2006.01) | |
| *A61B 5/021* | (2006.01) | |
| *G16H 10/60* | (2018.01) | |
| *G06N 20/00* | (2019.01) | |
| *G06N 7/00* | (2006.01) | |
| *G06N 20/20* | (2019.01) | |
| *A61B 5/024* | (2006.01) | |
| *A61B 5/053* | (2006.01) | |
| *A61B 5/08* | (2006.01) | |
| *A61B 5/145* | (2006.01) | |
| *A61B 5/01* | (2006.01) | |
| *A61B 5/026* | (2006.01) | |

(52) U.S. Cl.
CPC ........ *A61B 5/02055* (2013.01); *A61B 5/0402* (2013.01); *A61B 5/0488* (2013.01); *A61B 5/11* (2013.01); *A61B 5/681* (2013.01); *A61B 5/6823* (2013.01); *A61B 5/6898* (2013.01); *A61B 5/7203* (2013.01); *A61B 5/7267* (2013.01); *A61B 5/7278* (2013.01); *A61B 5/747* (2013.01); *A61B 7/04* (2013.01); *G06F 19/3418* (2013.01); *G06N 7/005* (2013.01); *G06N 20/00* (2019.01); *G06N 20/20* (2019.01); *G16H 10/60* (2018.01); *A61B 5/01* (2013.01); *A61B 5/021* (2013.01); *A61B 5/0261* (2013.01); *A61B 5/02416* (2013.01); *A61B 5/02438* (2013.01); *A61B 5/0533* (2013.01); *A61B 5/0816* (2013.01); *A61B 5/1128* (2013.01); *A61B 5/14542* (2013.01); *A61B 5/6814* (2013.01); *A61B 5/6816* (2013.01); *A61B 5/7207* (2013.01); *A61B 2562/0219* (2013.01)

(56) References Cited

U.S. PATENT DOCUMENTS

| | | | | |
|---|---|---|---|---|
| 2007/0100214 | A1* | 5/2007 | Steinert | A61H 1/00 600/300 |
| 2010/0113898 | A1* | 5/2010 | Kim | A61B 5/0261 600/310 |
| 2011/0245633 | A1* | 10/2011 | Goldberg | A61B 5/681 600/301 |
| 2015/0119746 | A1 | 4/2015 | Conradsen | |
| 2016/0213261 | A1* | 7/2016 | Fleischer | A61B 5/7267 |
| 2017/0027812 | A1* | 2/2017 | Hyde | A61H 23/004 |
| 2017/0136265 | A1* | 5/2017 | Hyde | G16H 50/30 |

OTHER PUBLICATIONS

Conradsen et al. (2009) "Multi-modal intelligent seizure acquisition (MISA) system—A new approach towards seizure detection based on full body motion measures," In; The Proceedings of the Annual International Conference of the IEEE Engineering in Medicine and Biology Society, 2009. EMBC 2009. pp. 2591-2595.

Cortes et al. (1995) "Support-vector networks," Machine Learning. 20(3):273-297.

Evrengül et al. (2005) "Time and frequency domain analyses of heart rate variability in patients with epilepsy," Epilepsy Research. 63:131-139.

Hoppe et al. (2007) "Accuracy of Patient Seizure Counts," Arch. Neurol. 6411:1595-1599.

Lockman et al. (2011) "Detection of seizure-like movements using a wrist accelerometer," Epilepsy Behav. 20(4):638-641.

nesmax.com (Sep. 4, 2015) "Collar Can Tell When Your Pet Is Sick," The Associated Press. Accessible on the Internet at URL: http://www.newsmax.com/Health/Health-News/collar-pet-health-petpace/2015/09/04/id/673605, 5 pgs. [Last Accessed Sep. 16, 2015].

Ng et al. (2002) "On discriminative vs. generative classifiers: A comparison of logistic regression and naive bayes," Inl the Proceedings of the Advances in Neural Information Processing Systems 14 (NIPS 2001). pp. 841-848.

Nijsen et al. (2005) "The potential value of three-dimensional accelerometry for detection of motor seizures in severe epilepsy," Epilepsy & Behavior. 7(1):74-84.

Pet Pace "Can the Collar be Used to Monitor Seizures?" PetPace. com. [Last Accessed Sep. 16, 2015] 1 pg.

Poh et al. (2012) "Convulsive seizure detection using a wrist-worn electrodermal activity and accelerometry biosensor," Epilepsia. 53(5):93-7.

Van De Vel et al. (Jun. 2013) "Non-EEG seizure-detection systems and potential SUDEP prevention: State of the art," Seizure. 22(5):345-355.

\* cited by examiner

PROOF-OF-CONCEPT PROTOTYPE.

FIG. 3

EXAMPLE HEART RATE SIGNAL DERIVED FROM PPG TAKEN AT THE WRIST.

FIG. 4

CHARACTERISTIC LEARNING CURVES OF GENERATIVE AND DISCRIMINATIVE CLASSIFIERS:
GENERATIVE CLASSIFIERS HAVE LOWER GENERALIZATION ERROR FOR SMALL TRAINING SETS,
BUT THEIR ASYMPTOTIC ERROR EXCEEDS THAT OF DISCRIMINATIVE CLASSIFIERS.

DIAGRAM OF HYBRID GENERATIVE-DISCRIMINATIVE CLASSIFIER WITH ACTIVE LEARNING

SYSTEM AND METHOD FOR IDENTIFYING ICTAL STATES IN A PATIENT

CROSS-REFERENCE TO RELATED APPLICATIONS

This application claims the benefit of priority to U.S. Patent Application Ser. No. 62/276,203, filed Jan. 7, 2016, which is incorporated by reference herein in its entirety.

U.S. GOVERNMENT RIGHTS

This invention was made with government support under NSF Grant No. 1112753 awarded by the National Science Foundation. The government has certain rights in the invention.

BACKGROUND

At least five million people in the United States and fifty million people worldwide suffer from epilepsy. Of these, thirty percent or more have poorly controlled seizures, a condition known as refractory epilepsy, despite treatment with medications and surgery. For most epilepsy sufferers selecting the anti-epileptic drug(s) and dosages that minimize seizure rate and side effects, while maximizing quality of life, requires a long trial and error process. When drug regimens are changed, the patient is hospitalized for several days of twenty-four hour monitoring to determine seizure rate under new medications. Once out of the hospital, seizure tracking relies on self-reporting by patients and their families if available, often taking form of seizure diaries. Unfortunately, many patients are unable to determine or remember that they have had a seizure, leading to underreporting of seizure rates by fifty percent or more. While seizures can be accurately diagnosed using electro-encephalography (EEG) synchronized with video monitoring, such "video-EEG" monitoring is expensive, not portable, and requires expert operation and review to identify seizures. This limits video-EEG to the inpatient setting, although most seizures occur outside this setting. These factors hinder efforts to assess whether new therapeutic regimens actually reduce seizure rates.

SUMMARY

A continuously wearable device detects and records epileptic seizures during normal patient routines. The device uses a plurality of extra-cerebral sensor modalities coupled with a responsiveness test. Extra-cerebral signals for example include limb acceleration, pulse photoplethysmography (PPG), measures of blood pressure, heart rate, oxygen saturation level, and respiration rate derived from PPG, acoustic signals from microphones that record vocalizations, electro-cardiogram (ECG) signals, electromyography (EMG), eye motion, facial motion, and galvanic skin response (GSR). Alternative embodiments may combine some or all of these sensors.

In an embodiment, a system identifies ictal states in a patient, the system includes a processing unit and a plurality of different non-electroencephalographic sensors configured to sense signals from the patient. The processing unit has a processor and memory with instructions for deriving feature vectors from the plurality of sensors and classifying the derived feature vectors to determine probability of the patient being ictal, when the probability is sufficiently high asking the patient if the patient is in an ictal state, logging or counting the seizure and/or reporting to a caregivers if the patient is ictal, and updating the classifier based upon sensor data, probability, and the response.

In another embodiment, the method for identifying ictal states includes sensing, using a plurality of non-electroencephalographic sensors configured to sense signals from the patient, deriving feature vectors from the plurality of sensors and using a classifier trained using a training dataset, to determine the probability of the patient being in an ictal state, and if the probability is sufficiently high, asking the patient if the patient is in ictal state, reporting ictal states to caregivers, and updating the classifier.

DETAILED DESCRIPTION OF THE EMBODIMENTS

Seizures fall into two general categories, each of which manifests itself in a range of behaviors. Generalized seizures involve the whole brain, and the patient loses consciousness at the onset of the seizure. Manifestations range from convulsions (stiffening of the body with jerking limbs as in a tonic-clonic 'grand mal' seizure) to 'petit mal' or absence seizures where the patient enters a trance-like state. Loss of muscle tone can also occur during generalized seizures, which thus induce falls. Sudden, aperiodic muscle jerks are characteristic of myoclonic manifestations. Partial seizures, on the other hand, begin in one area of the brain. Complex partial seizures may include impaired consciousness with altered awareness, confusion, jerking of limbs, perceptual disturbances (sight, hearing, smell, taste) or auras. Simple partial seizures can include motor, sensory, and autonomic symptoms with unimpaired consciousness, although speech can be inhibited for the duration of the seizures. Partial seizures can progress to generalized seizures. Repetitive vocalizations, lip smacking, and facial motions can accompany both partial and generalized seizures.

Current epileptic seizure diagnosis is focused on analysis of EEG signals obtained clinically. Electrodes are placed on the scalp and changes in voltage are detected at the surface of the scalp with excellent temporal specificity. An effective approach to prescribing appropriate antiepileptic medication(s) and determining the efficacy of treatment often involves a lengthy inpatient hospital stay with twenty-four hour surveillance. A neurologist, utilizing a video camera synchronized with an EEG (video-EEG), is able to identify the type, frequency and severity of seizures a patient has while hospitalized.

Studies have applied machine learning to EEG signals to detect onset of an ictal (seizure) state and its duration. For example, patient-specific classifiers have been constructed for scalp EEG data using feature-based machine learning. Features are derived from EEG signals and a combination of EEG and electrocardiogram (ECG) signals based on spectral frequency components are identified from time-domain data; and a support vector machine classifies the feature vector derived from a data epoch or sequence of observations into a binary class—ictal or non-ictal state. Similar approaches to using EEG for seizure detection have used different feature vectors in the classification approach. Automatic seizure detection using EEG signals alone is overly sensitive to patient motion and other artifacts and therefore is ineffective outside of the clinical setting. Thus, there is a need to detect seizures during normal routine to reduce the incidence of unreported seizures and thereby improve the treatment of epilepsy.

Recent studies with controlled clinical conditions have shown promising results that ictal states can be statistically separated from normal homeostasis using single sensor modalities other than EEG. Variations in heart rate, breathing rate, and specific movements have been shown to correlate with seizures. Studies show heart rate increases by an average of ten beats per minute near seizure onset in 93% of eighty-one epileptic patients participating in a study and clearly preceding the seizure onset in 49% of patients. ECG abnormalities were also common, and one case of asystole (no cardiac electrical activity and contractions) was observed. Additionally, electrodermal response—a measure related to autonomic nervous system response—has been shown to correlate with seizures, although it also correlates with many other normal conditions as well (e.g., perspiration due to exertion, fear, dehydration). These approaches can potentially detect clinical as well as subclinical seizures, but they look for a single measurable index to indicate a seizure. However, it appears that the presentation of epilepsy is so diverse that no single metric can be sufficiently sensitive and specific for seizure identification during a patient's normal routine because normal activities can trigger false detection.

For purposes of this document, a photoplethysmographic (PPG) sensor is an optical sensor adapted to be placed on or near skin and adapted to measure one or more of blood oxygenation, pulse, cardiac arrhythmia, respiration rate, blood pressure, and cardiac pulse waveform. An ECG sensor is an electrical sensor having two or more electrodes adapted for placement on or near a person's chest to detect heart contractions electrically; in embodiments, the electrodes may be placed directly on the chest, or may be within an elastic band or similar device. ECG sensors are capable of monitoring at least pulse rate; in particular embodiments, they are adapted to detect cardiac arrhythmias and other changes in cardiac function. An electromyography (EMG) sensor is an electrical sensor having two or more electrodes that record electrical activity from muscles. Certain optical sensors may serve as proxies to EMG sensors to avoid, for example, placement of electrodes on the face to monitor facial motions. Certain optical sensors or cameras may also track eye motion.

Our device uses machine-learning algorithms that incorporate patient response to queries in state classification, while using multiple sensor types. Traditional machine-learning techniques seek to maximize classification of true positive and negative events and minimize false positive and negative classifications. In the context of seizure detection, the goal of such techniques would be to count seizure events with extremely high accuracy based solely on sensed extra-cerebral signals. In contrast, our machine-learning techniques work in two stages: generate preliminary seizure classifications by processing extra-cerebral signals, and then seek additional input through a patient responsiveness test to increase the classification accuracy. In other words, the device of the invention mimics what a human caregiver would do upon observation of a possible seizure—for example asking the patient "Are you having a seizure?" The lack of response affirms the seizure to high probability owing to seizure amnesia. If the patient is experiencing a partial seizure without alteration of responsiveness, she or he could also confirm this.

Such queries are "costly" in the sense that they cannot be made continuously without excessively intruding on the patient and thus must be conditioned upon a reasonable preliminary classification. However, they provide definitive classification for medical conditions where inability to respond is a major characteristic, such as epilepsy, concussion, near-fatal fall, heart attack, et cetera. The query response also becomes a state label of the data (seizure, no seizure), for which sparsely supervised machine learning techniques may be used that retrain an existing classifier with new, patient-specific data obtained during normal routine outside of a clinical setting (in a process known as active learning). Consequently, a classifier developed based on training data from a limited patient pool and controlled clinical conditions becomes progressively more accurate for each individual patient in real-world settings.

Unobtrusive extra-cerebral sensors, combined with novel machine-learning algorithms that include an interactive element, are used to create a wearable device to accurately detect and record seizures outside of the clinical setting. The device provides for accurate seizure counting and tracking to optimize therapeutic regimes, real-time caregiver notifications to improve patient safety and well-being, and a large database of physiological and behavioral data associated with seizures assisting new understanding and treatment of epilepsy. But beyond epilepsy, there is broad applicability of the device and associated machine-learning techniques to the treatment and care of individuals with other medical conditions that hinge on event detection during normal routine.

We therefore make use of multiple, extra-cerebral signals that are likely to change in concert during seizures. Exclusion of EEG signals frees us from a clinical setting and makes packaging simple enough to allow for continuous, everyday, wear by the patient. We use machine-learning techniques based on time-series, multi-modal data to classify seizures against the background of normal activity.

Studies have shown that many physiological measures—heart rate, respiration rate, oxygen saturation level, and pulse wave velocity—a measure related to blood pressure—may be derived from the waveform of a photoplethysmographic (PPG) sensor, which is commonly worn on the finger, earlobe, or forehead. While signals from PPG sensors are sensitive to motion artifacts, inclusion of direct measures of motion assists in rejecting these motion artifacts from the PPG.

Figure 1:
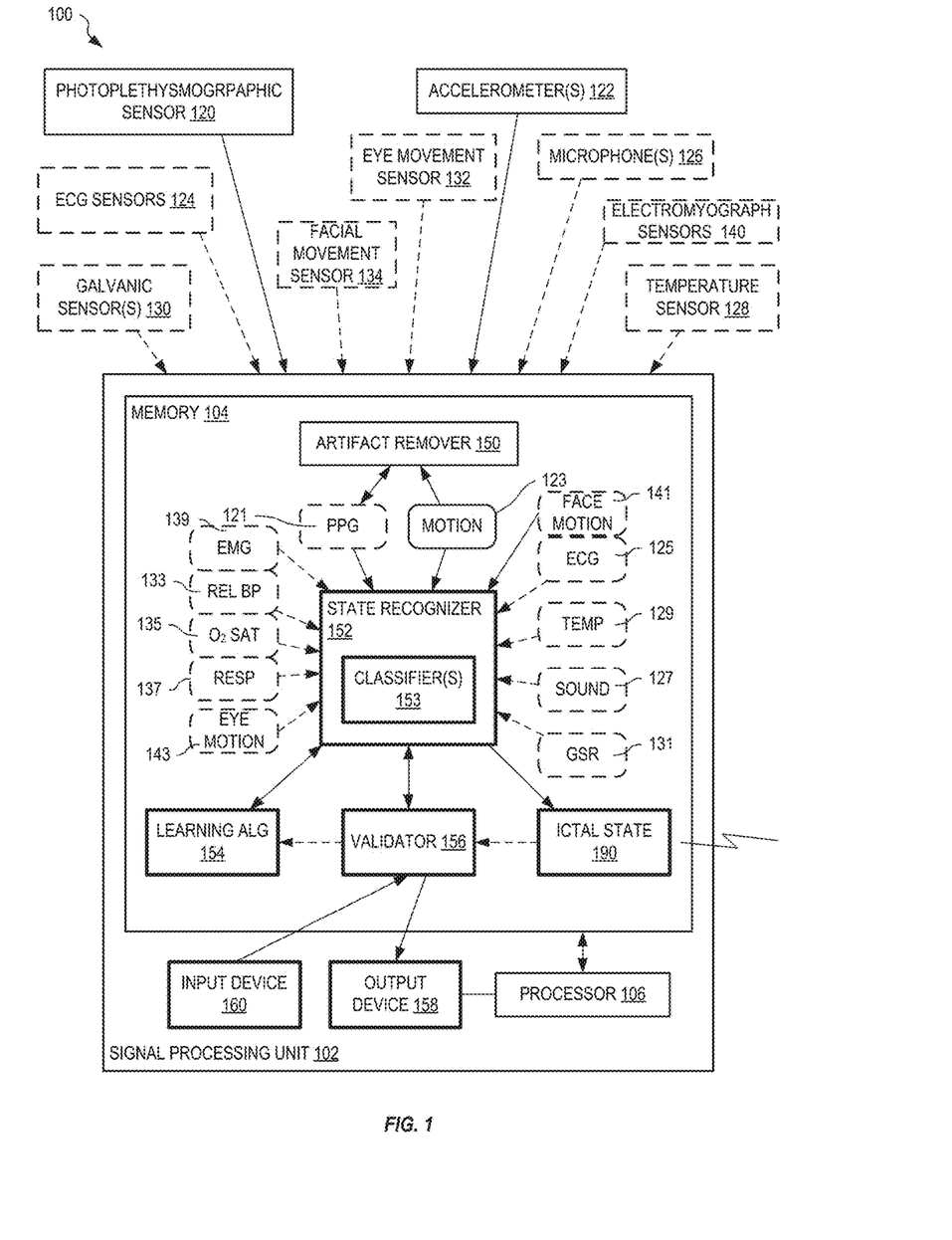
FIG. 1 shows one exemplary system for identifying ictal states in a patient, in an embodiment.

FIG. 1 shows one exemplary system 100 for identifying ictal states in a patient. System 100 includes a signal processing unit 102, and a plurality of sensors that includes at least two of the following sensors: PPG sensor 120, accelerometer 122, electrocardiogram (ECG) sensor 124, a microphone 126, a temperature sensor 128, a galvanic skin response (GSR) (also known as electrodermal activity (EDA) or electrodermal response) sensor 130, electromyography (EMG) sensor 140, an optical facial muscle motion sensor (134), and optical eye motion tracking sensor (141). Signal processing unit 102 includes a memory 104 and at least one processor 106 communicatively coupled with memory 104. In embodiments, the ECG sensor 124 includes a two-electrode sensing unit; in alternative embodiments, the ECG sensors 124 include additional electrodes.

In an embodiment, optical eye movement sensors 132 mounted to an eyeglass frame or cap brim are provided. In embodiments, electromyographic sensors 140 adapted to detect movements of muscles known to be involved in a particular patient's seizures, are provided. In some embodiments, an optical sensor 134 or camera is positioned on a cap brim or mounted to an eyeglass frame to observe movements of facial muscles.

As shown in FIG. 1, sensors 120-134 operate to send sensed data 121, 123, 125, 127, 129, 131, 133, 135, 137, 139, 141, and 143 to signal processing unit 102, where it is processed as received and/or stored within memory 104 for further processing; in most embodiments processing occurs in or near real time so that verification questions can be presented to the wearer during a seizure, not after it has ended. Signal processing unit 102 includes a state recognizer 152, implemented as machine readable instructions (software) stored within memory 104 and executed by processor 106, that identifies ictal states in patient 202 (FIG. 2) based upon two or more of PPG data 121, limb motion data 123, ECG data 125, sound data 127, temperature data 129, GSR data 131, eye motion data 143, relative blood pressure data 133, $O_2$ saturation data 135, EMG data 139, eye movement data 132, facial muscle data 141, and respiration rate 137 using one or more classifiers 153. Signal processing unit 102 also includes an artifact remover 150, implemented as machine-readable instructions stored within memory 104 and executed by processor 106, to remove motion artifacts from sensed PPG data 121 based upon motion data 123 and to bandpass filter sensor signals from sensors 120-134.

In FIG. 1, state recognizer 152 includes machine-readable instructions for deriving feature vectors from sensor data and an ensemble of generative and discriminative classifiers embodied as machine-readable instructions for classifying feature vectors into ictal or non-ictal states.

Figure 2:
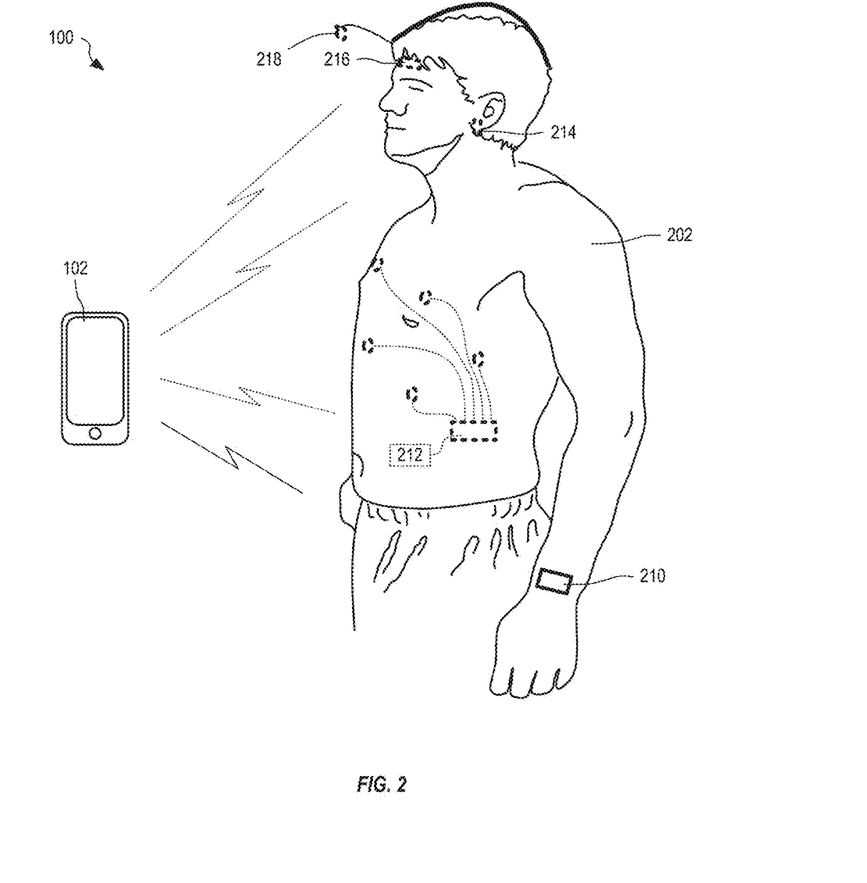
FIG. 2 shows the system of FIG. 1 configured with one or more sensor modules, each containing at least one sensor, that unobtrusively attach to a patient, in an embodiment.

FIG. 2 shows system 100 of FIG. 1 configured with one or more sensor modules (e.g., wrist module 210, chest module 212, ear module 214, and forehead module 216), each containing at least one sensor (e.g., one or more of sensors 120-134), that unobtrusively attach to a patient 202, senses signals from the patient, and transmit sensed data to signal processing unit 102, through a wired or wireless connection. Each module may contain a low powered wireless transceiver implementing one or more wireless protocols such as Bluetooth, Bluetooth LE, Zigbee, ANT, and other protocols. In an alternate embodiment, signal processing unit 102 and the one or more modules 210, 212, 214, and 216 communicate through a wired connection.

In one exemplary implementation, module 210 is built into a watch worn by patient 202. In another exemplary implementation, module 212 is incorporated into a vest that is worn by patient 202. In another exemplary implementation, module 214 is incorporated into a headset worn by patient 202. In another exemplary implementation, module 216 is incorporated into a hat or visor that is worn by patient 202. System 100 may include other modules for positioning sensors at/on other parts of patient 202 without departing from the scope hereof. System 100 may also utilize multiple modules concurrently, where each module incorporates one of more sensors 120-134. In the example of FIG. 2, signal processing unit 102 is implemented using a smart phone or other similar communication device. In one embodiment, signal processing unit 102 logs, including counting, sensed ictal states of patient 202. In particular embodiments, signal processing unit 102 also communicates a sensed ictal state of patient 202 to a caregiver directly, or indirectly through another device such as a cell phone or body area network (BAN) master node, using one or more of Bluetooth, IEEE 802.11 Wi-Fi, local area networks, cellular network using short message service (SMS) and/or email, and the Internet. FIGS. 1 and 2 are best viewed together with the following description.

In a first embodiment, system 100 includes 3-axis accelerometer (3AA) sensors 122 and electrocardiogram (ECG) sensors 124; in a particular embodiment the system further includes one or more additional sensors selected from a photoplethysmographic (PPG) sensor, a GSR sensor, a microphone, a temperature sensor, a facial movement sensor, an EMG sensor, and an eye-motion sensor.

In a second embodiment, system 100 includes 3AA sensors 122 and electromyographic (EMG) sensors; in a particular embodiment, the system further includes one or more additional sensors selected from a photoplethysmographic (PPG) sensor, a GSR sensor, a microphone, a temperature sensor, a facial movement sensor, an ECG sensor, and an eye-motion sensor.

While some of our sensors (such as eye movement sensors mounted on a cap visor or glasses frame) are linked to the processing unit by short-range digital radio, other sensors may in some embodiments be directly connected to a processing unit. For example, in a particular embodiment of FIG. 3, GSR sensors, accelerometers, a microphone, and PPG sensing are integrated with a processing unit attached to a patient's body.

Signal processing unit 102 also includes a validator 156, implemented as machine-readable instructions stored within memory 104 and executed by processor 106 and coupled to an audio transducer (such as a loudspeaker) or other signaling device 158, that interrogates patient 202 when ictal state 190 indicates a seizure to validate that the seizure is occurring. For example, upon detecting ictal state 190, validator 156 asks whether patient 202 is having a seizure. The patient 202 may respond verbally through microphones 126 or through an input device 160. If patient 202 does not respond within a timeout period, validator 156 assumes that the determined ictal state 190 is correct; otherwise validator 154 evaluates the response from patient 202 and determines whether ictal state 190 is, or is not, a false positive.

Signal processing unit 102 may include a learning algorithm 154, implemented as machine-readable instructions stored within memory 104 and executed by processor 106, to improve reliability of state recognizer 152 based upon determined ictal states 190 and validation by validator 156 and an active learning technique described in further detail below.

Figure 3:
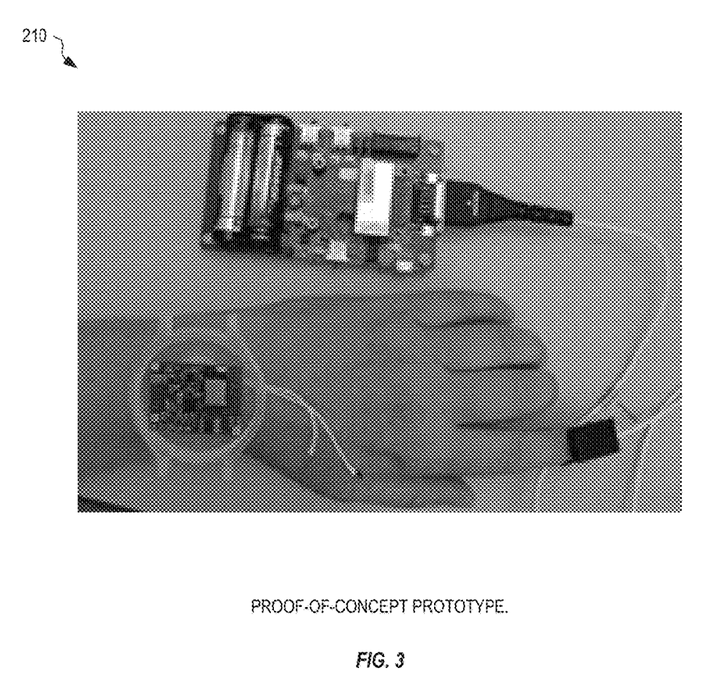
FIG. 3 shows one exemplary prototype of the system of FIG. 1 operating to monitor and record PPG, three-axis motion, electrodermal response, skin temperature, and frequency content of vocalizations, in an embodiment.

FIG. 3 shows one exemplary prototype of system 210 that operates to monitor and record PPG (e.g., PPG data 121), three-axis motion (e.g., motion data 123), electrodermal response (e.g., GSR data 131), skin temperature (e.g., temperature data 129), and vocalizations (e.g., sound data 127). The prototype of system 210 includes a PPG sensor (e.g., PPG sensor 120) and circuit board, skin temperature sensor 128, accelerometers 122, a wrist-worn sensor module (e.g., wrist module 210), and a microphone (e.g., microphone 126). By implementing signal processing unit 102 as a commercially available mobile device (e.g., smart phone), features such as GPS location, voice recognition, email and SMS communications, and emergency communications are readily available to enable communication with healthcare professionals and a patient's caregivers. In FIG. 3, the circuit board within the watch-like housing incorporates accelerometers 122, skin temperature sensing 128, and electrodes for measuring skin galvanic response 130 (white wires), which contact the wearer (e.g. patient 202) on the skin underneath the housing. In a particular embodiment, PPG sensor 120 is worn on the fingertip; but in alternative embodiments PPG sensor 120 is worn on the earlobe (e.g., within module 214), forehead (e.g., within module 216) or wrist (e.g., within module 210). Integrating accelerometers 122 into limb modules such as wrist module 210 allows limb motion to be measured and allows artifact remover 150 to correct for motion artifacts within PPG data 121. Where present, an optical eye movement sensor may be mounted either to a cap brim 218 or to an eyeglass frame (not shown) worn by the patient, the eye movement sensor within a module linked to the processing unit by short-range radio. In some embodiments, a facial movement sensor is also mounted to the cap brim, and may share components such as a camera with the optical eye movement sensor.

Figure 4:
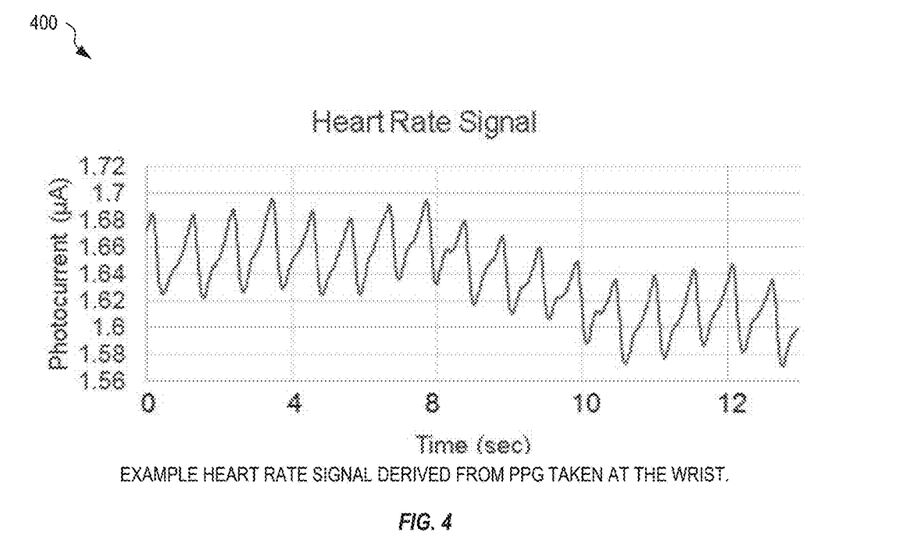
FIG. 4 shows an example of a heart rate signal derived from PPG obtained at the wrist.

In an embodiment, the disclosed invention integrates a plurality of sensors into sensing modules that are worn on one or both wrists, providing redundancy in measurements, and incorporates microphone signals and a transducer (speaker) for interacting with the patient 202. FIG. 4 shows an example of a heart rate signal obtained at the wrist using a wrist-worn sensor module. The current from the PPG photoreceptor is processed by an ultralow-noise, signal-conditioning path to obtain a clean heart rate signal. FIG. 4 shows the quality of signals that can be derived from wrist PPG using state-of-the-art technology. Using concurrent ECG, PPG, and accelerometers and/or other sensors enables system 100 to derive features that correspond to seizure-related events and enable us to separate those states from normal activities, such as exercise and sleep, as described below.

In an embodiment, machine-learning processes multimodal extra-cerebral signals using sparse supervision to train a classifier from training data gathered from a population of patients, and then subsequently tailors itself over time for each individual using active learning—an approach that incorporates new labeled data to improve a classifier over time. Our approach addresses open problems in machine learning that are characteristic of seizure detection. These problems include classification of infrequent events from time-series data (i.e., events with low frequency of occurrence relative to normal events); classification of events whose statistical variation may overlap significantly with normal events; classification of events that may elicit different behaviors in different segments of a population (e.g., exacerbation of gross motor behavior in grand mal seizures versus quieting of motion as in a petit mal seizure); generalization of a trained classifier for one or a few individuals having a medical condition to a population of individuals with a similar condition; personalization of a classifier over time to improve its performance; and feature vector selection for optimizing classification accuracy. Additionally, we use data acquired clinically to train classifiers and then extend the classifiers to settings outside of the clinic. Outside of the clinic, non-ictal states exhibit wider statistical variation than those observed within the clinic, where the patient is confined to a bed.

Machine learning algorithms are generally categorized by at least three parameters—supervised versus unsupervised, active versus passive, and online versus batch learning. In supervised learning, labels y exist for a training dataset of feature vectors or inputs x, and these training examples are used to build a classifier. Unsupervised learning draws inferences or conclusions about inputs without associated labels. Active learning incorporates experiments or queries to learn from the environment, while passive methods can only observe inputs and cannot influence these inputs. Online learning requires the learner to learn as inputs are being collected, while batch learning generally implies that a large dataset is available from which to build a classifier.

Regarding classifier performance, a true positive corresponds to accurately classifying a particular event or behavior (e.g., classifying a seizure as a seizure or ictal state), and a true negative corresponds to accurately classifying a non-ictal state. In order to achieve acceptable true positive and negative classification rates, as is common in machine learning, a tradeoff exists with false positive and negative rates. That is, achieving high true classification rates generally incurs less than acceptable false positive (false alarm) and/or false negative (missed seizure) classification rates. In an embodiment, our seizure detection is a hybrid of supervised and unsupervised learning, active learning, and online and batch learning owing to the characteristics noted above—classification of infrequent events, the amount of training data available, and the need to operate robustly outside of the clinic.

In order to derive labeled training data for machine learning, one needs an "expert" or "gold standard" to label data, in our case, as an ictal or non-ictal state. Our training data consist of the physiological measures, audio, and limb accelerations obtained using body-worn sensors as described above. Typically, such data is obtained clinically, for a small number of patients using video-EEG monitoring synchronized with acquisition of body-worn data. The video-EEG data are then labeled and the labels are transferred to sensor data. In this way, we obtain gold-standard ictal state and non-ictal state training examples for a small population of epilepsy patients.

Not only is the labeled dataset small, but it is also acquired in the clinic; hence, the non-ictal states are biased towards those acquired when activity is limited (mainly resting in a hospital bed). We augment this dataset with data acquired outside of the clinic, but from non-ictal states only, as, until our system is deployed, there is no inexpensive and feasible way of labeling ictal states outside of the clinic in order to provide more general training data. Given this dataset, the objective of machine learning is to provide a classifier that identifies seizures robustly for the population.

System 100 implements a supervised machine learning approach that triggers active learning based on a classification probability threshold and incorporates bootstrapping, which improves the classifier for the individual over time.

Figure 5:
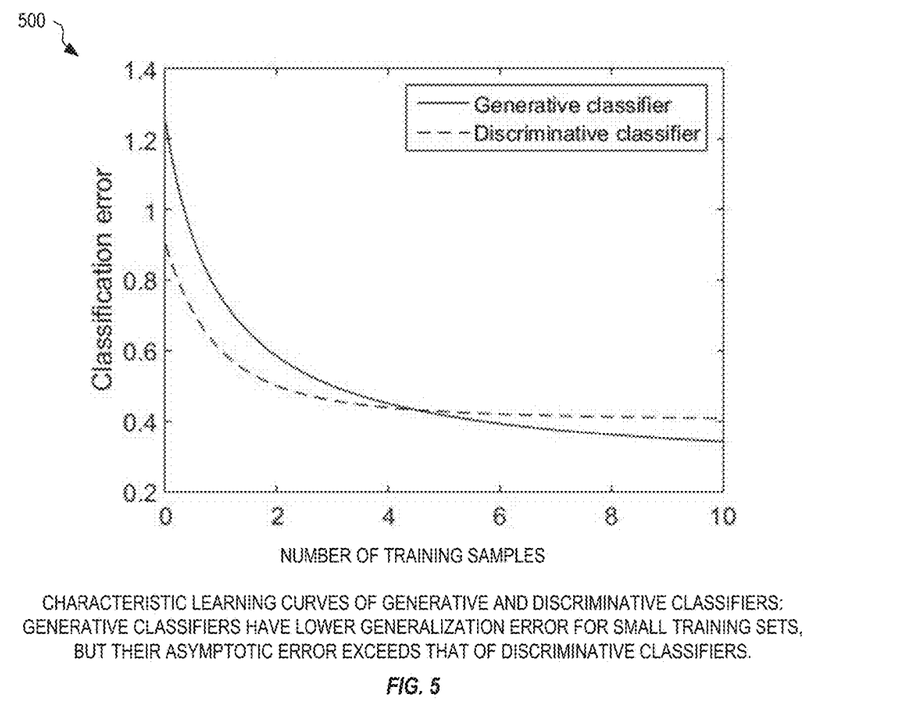
FIG. 5 shows an exemplary comparison between a generative and discriminative approach for binary classification.

Generative approaches learn a model of the joint probability p(x,y) of inputs x and labels y. Using this model, Bayes' rule can be used to calculate the conditional probability p(y|x) in order to predict labels for new data. Training data are used to supervise learning of the model. Discriminative classifiers learn the conditional probability directly from training data and thus provide a map from data to labels for new, unlabeled data. FIG. 5 shows an example comparison between a Naïve Bayes classifier and a logistic regression—a generative and discriminative approach, respectively, for binary classification. The generative approach reaches its asymptotic error faster and with fewer training examples compared with discriminative classifier; however, the discriminative classifier has lower asymptotic error overall, given a sufficiently large number of training examples. The example of FIG. 5 illustrates this. In the context of classifying seizure state based on physiological measures, the distinction is important because the training set includes many more non-ictal than ictal states (i.e., ictal states are relatively more rare compared with normal states). With limited training data, generative classifiers are normally more accurate, but with a wealth of data and a more balanced data set than we expect, discriminative classification is best.

System 100 implements an ensemble of generative-discriminative classifiers whose output comprises conditional probabilities of ictal and non-ictal states generated both using a model (generative) and by direct mapping (discriminative). Together, the estimates of conditional probability are used to trigger (or not) the acquisition of additional input data from queries or interaction with the patient—a form of active learning—from which the conditional probability of a class label is recalculated. In other words, system 100, upon detecting a sufficiently high conditional probability of an ictal state (but not necessarily one above 90%) can, using validator 156, ask patient 202 directly "Are you having a seizure?"—and absence of a response provides strong indication of an ictal state. For patients who have partial seizures without alteration of responsiveness, the query may be useful to confirm whether behavioral changes represent a typical seizure for patient 202. This interactive element of the classifier is not one that can be "active" with each sample of data gathered, or even periodically with a high frequency, synchronous or asynchronous with data collection, owing to the obtrusive nature of such interaction. In other words, if one were to ask the patient every ten minutes "Are you having a seizure?" the device would be unacceptable from a human-centered design standpoint. However, upon establishing a likelihood threshold, queries are less frequent, resolve true positives from false positives, and provide labeled data to improve classification performance for the individual based on the body-worn sensor suite of system 100. The approach uses online learning to tailor the classifier to the individual.

Figure 6:
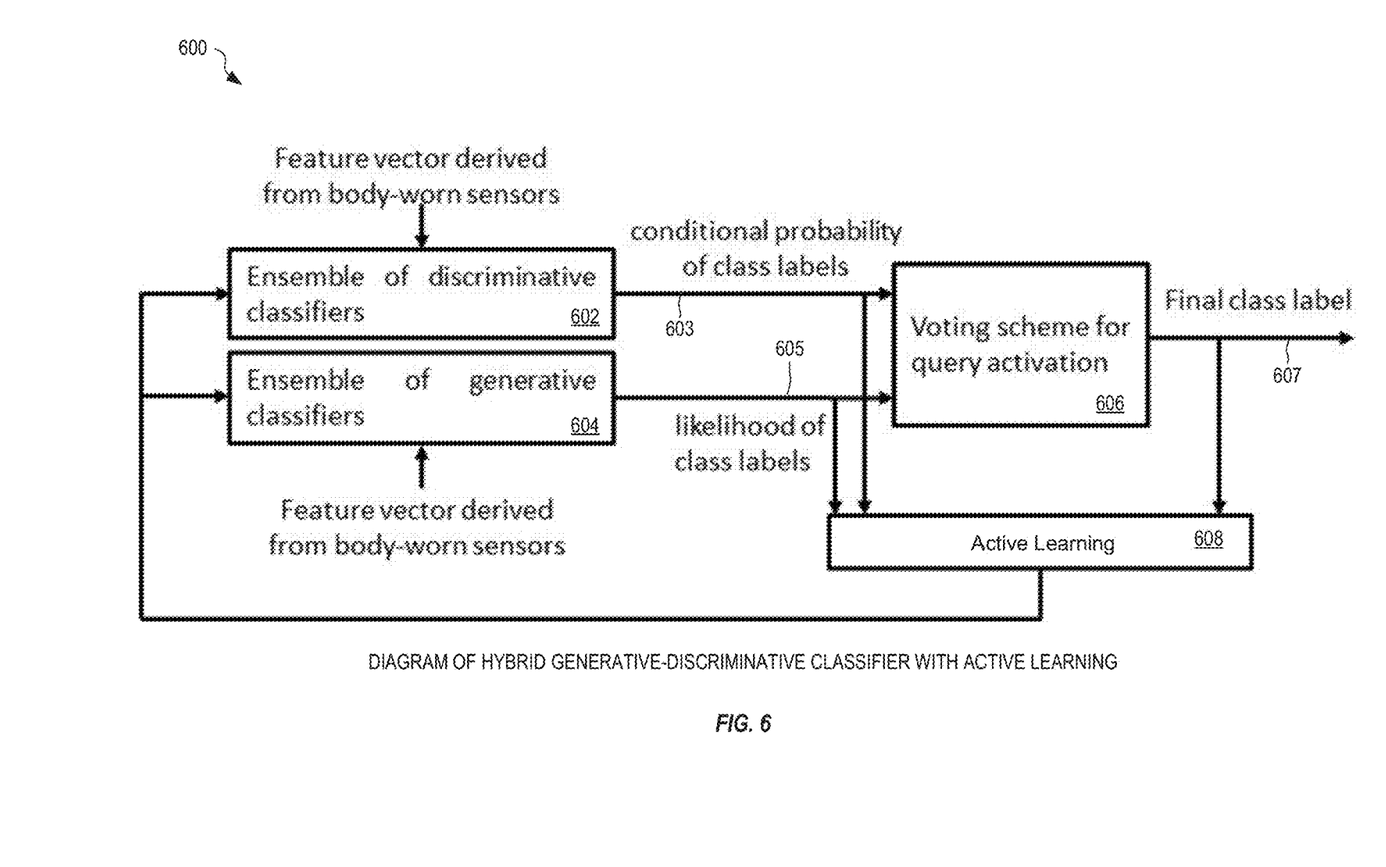
FIG. 6 is a flow diagram that illustrates one exemplary method for a hybrid generative-discriminative classifier with active learning, in an embodiment.

FIG. 6 is a flow diagram that illustrates one exemplary method 600 for a hybrid generative-discriminative classifier with active learning. On the left side are ensembles of generative 602 and discriminative 604 classifiers trained on sparse hand-labeled training data acquired clinically, each providing a conditional probability 603 or likelihood 605 of a class label given a feature vector derived from a time epoch of body-worn sensors (physiological measures and vocalizations). Given the separate labels from each classifier, a fusion or voting scheme 606 provides a fused class label 607 along with a decision of whether to activate a query. If there is moderate to strong indication of an ictal state, a query is made "Are you having a seizure?", and the response confirms (or not) the initial label. The final class label 607 fuses the outputs of the two classifiers and the query output. The query provides an independent "hand label" of the data, and those data are used in active learning 608 to update the classifier, tuning it to the individual. In this way, if the false positive rate of the initial classifiers is too high, it improves over time to detect fewer false positives.

This approach targets use of sensors from multiple sensing modalities in which the combination of features that provides the best classification for a particular patient may be unknown in advance. An open question for detection of behaviors or states based on time-series data is that of selection of such feature vectors, i.e., attributes from which the state may be detected with high probability. Our physiological measures consist of time-series data gathered from discrete sensors (e.g., sensors 120-134) and including acoustic signals (sound 127) from microphones 126. Using a plurality of sensors allows for simpler machine learning elements 602 and 604, such as support vector machines, logistic regression, naïve Bayes, and linear discriminant analysis to be used to classify the data in real time, as statistical separability is achieved through the plurality of sensors.

Figure 7:
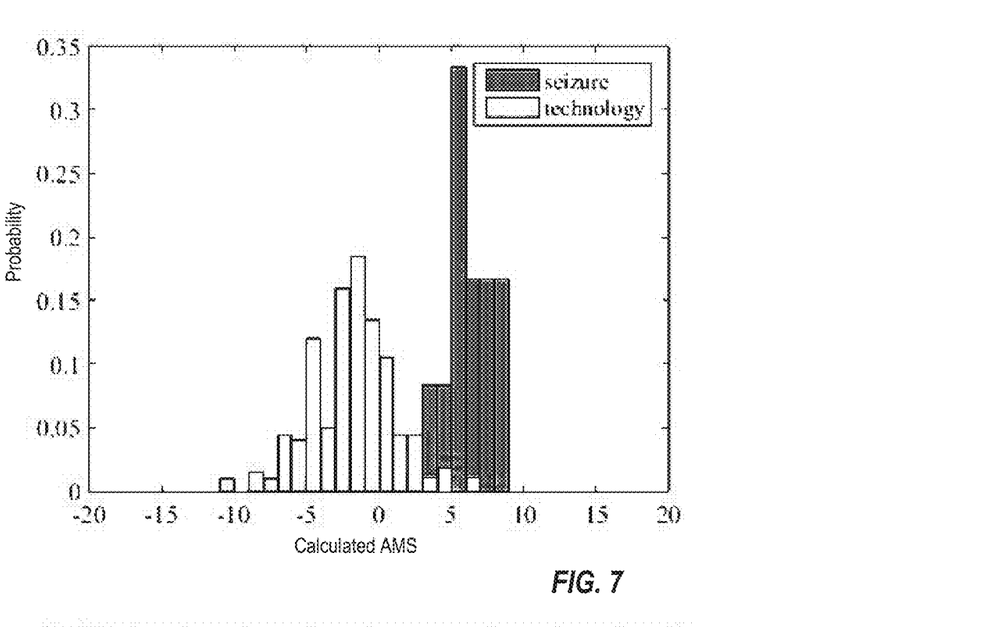
FIG. 7 illustrates one exemplary histogram of calculated axis of maximal separation (AMS) versus the probability density function using a plurality of extra-cerebral sensors for twelve epochs of seizure data and two hundred randomized epochs of data obtained while the patient is using technology (phone, computer).

FIG. 7 shows example results of classification of ictal states and other "activities" from extra-cerebral sensors acquired within a clinical setting. Transducers included ECG, audio, galvanic skin response (GSR), EMG, and tri-axial acceleration. A three-lead ECG was placed on the patient's chest, the microphone was placed on a table next to the patient, and the remaining sensors were fitted into a sleeve donned on the left arm. Microphone signals were sampled at fifty kHz to record high fidelity audio, and remaining signals were sampled at five kHz to meet Nyquist sampling criteria for all other signals. The medical staff simultaneously acquired EEG, ECG, and oxygen saturation as part of usual inpatient monitoring. Data were acquired for four patients. Each wore the device for at least seven hours and up to fifteen hours during their inpatient stay. One patient experienced four separate seizure events while wearing the device. Others had no seizures while wearing the device. The patients were continuously videotaped in the EMU. Data were synchronized with the video recording, and the EMU staff provided descriptions of patient activities from the time-stamped video data. Apart from times for epileptic events, the staff noted when patients slept, ate, talked, watched TV, used their phones or laptops, or temporarily removed the device. We evaluated statistical separability of the seizure events from four classes of non-seizure activities—talking, eating, sleeping, and using technology (e.g., phone, laptop, TV) based on 34 time- and frequency-domain features (chosen out of an initial set of 52 features). Features were extracted from five-second epochs of time-domain data after bandpass filtering the data to reduce noise, with two to eleven features extracted for each transducer. Salient transducer characteristics, as well as example features extracted, are summarized as follows:

Electrocardiogram (ECG): ECG measures heart rate (HR), heart rate variability, and cardiac repolarization abnormalities. Tachycardia (HR>100 beats/min) and bradycardia (HR<60 beats/min) are common autonomic responses to simple and complex partial seizures, and secondarily generalized seizures.

Surface Electromyogram (EMG): EMG records electrical response resulting from nerve stimulation of muscle. Forearm tension and relaxation due to myoclonic, atonic, myoclonic-atonic, epileptic spasms, and startle-induced reflex seizures can be clearly observed in the signal; thus, the electrodes for this sensor encompassed the patient's entire forearm.

Electrodermal Activity (EDA—as measured with a GSR sensor): The skin is innervated by the sympathetic nervous system, and many epileptic patients experience goosebumps, sweating, and skin color change during seizures. GSR can detect electrical changes on the skin's surface between two surface electrodes.

Tri-axial Accelerometer: Uncontrolled, convulsive, or repetitive movements of extremities are hallmarks of many seizures. Accelerometers track translational accelerations, which can identify idiosyncratic patterns for simple motor seizures. Similar to other seizure detection studies, the accelerometer is positioned in the middle of the patient's forearm.

Microphone: Dysphasia (impaired language production) and speech automatisms often occur during focal epileptic seizures. A microphone operating under a 100 ms ON/100 ms OFF duty cycle acquires vocalizations while maintaining patient privacy.

Photoplethysmography (PPG): PPG has been shown to detect variations in heart rate, blood pressure, cardiac output, oxygen saturation, and respiration rate, which are all physiological markers that can change during seizures.

Figure 8:
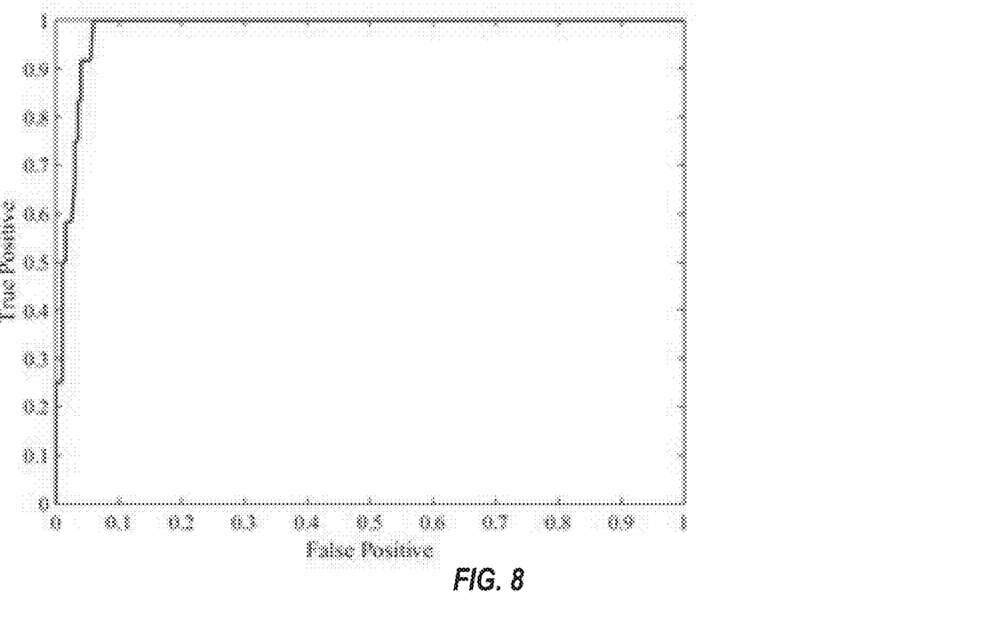
FIG. 8 illustrates a receiver-operator (ROC) curve for seizure versus technology use in the case of FIG. 7.
Figure 10:
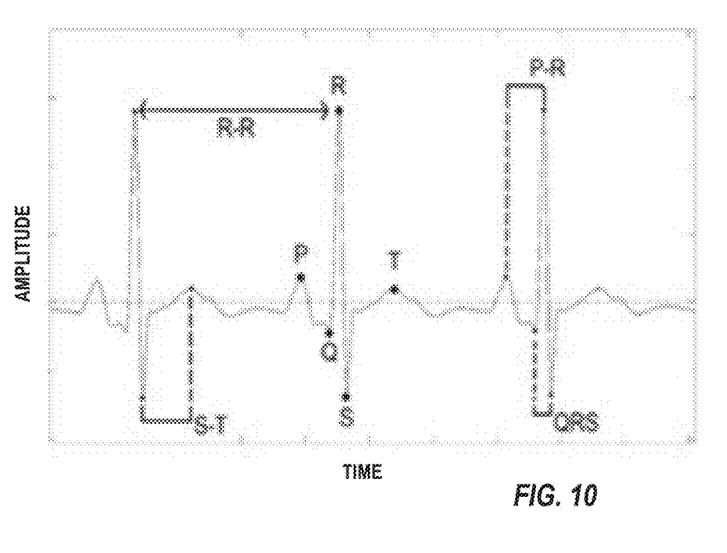
FIG. 10 shows the morphology of an ECG signal.

As an example of feature vector extraction from transducers, we detail ECG feature derivation. FIG. 10 shows the morphology of an ECG signal. The heart rate over a window of time is inversely proportional to the average R-R interval, or time between peaks in FIG. 2. Since tachycardia, bradycardia, and asystole can occur during a seizure, the mean R-R interval and its standard deviation are two features extracted from five-second epochs of this signal. The P wave occurs due to arterial depolarization, the QRS wave due to ventricular depolarization, and the T wave due to ventricular repolarization. The most serious seizure-related cardiac irregularities are ST-elevation/depression and T-wave inversion, both caused by abnormal ventricular repolarization during an epileptic event. Hence, we extracted the mean and standard deviation of signal values between S-T points. The T value and its standard deviation indicate whether that part of the wave has been inverted and provide additional features. Linear Discriminant Analysis (LDA) is used to evaluate separation between the four activity clusters and seizures. In LDA, the vector difference between the center (mean) of activity A epochs and the center of activity B epochs is computed. The corresponding unit vector is the axis of maximal separation (AMS). The data for each activity are projected onto the AMS to visualize the best-case linear separation within the feature space; separation of data along the AMS is representative of separation in 34-feature space. Histograms for epochs of each activity provide visualization of the projection onto the AMS and separability; the largest components of an AMS correspond to the features most important in separating data. Given the paucity of seizure data in this pilot study, the AMS is always calculated using the same twelve epochs of seizure data and a minimum of forty epochs of data from a given activity. We classified randomly selected epochs of activity data in order to include the effects of potentially nonstationary statistics in the analysis. Classifier performance is measured by the receiver operator curve (ROC), or true positive rate (sensitivity) versus false positive rate (1−specificity), i.e., by accurately classifying a seizure as a seizure and a non-ictal state as non-ictal, and associated false positive and negative rates. In machine learning, achieving high true classification rates often incurs less than acceptable false positive (false alarm) and/or false negative (missed seizure) rates. We found that the area under the ROC curve for seizure events and each activity ranged from a low of 0.985 (for seizure events versus two hundred randomized epochs from technology use activity) to 0.997 (for seizure events versus two hundred randomized epochs of talking); in other words, even in the highest overlap case between seizure data clusters and activity data clusters, normal activity is highly separable from seizure data given the multi-modal sensor suite and 34-element feature vector. Example histograms of the data separation for technology activity versus seizure are provided in FIG. 7, and the calculated ROC curve is shown in FIG. 8. Using additional technology activity data beyond the forty used to calculate the AMS did not significantly change the mean or standard deviation of the cluster, which provides a preliminary empirical measure of how much data are required to build a classifier.

Figure 9A:
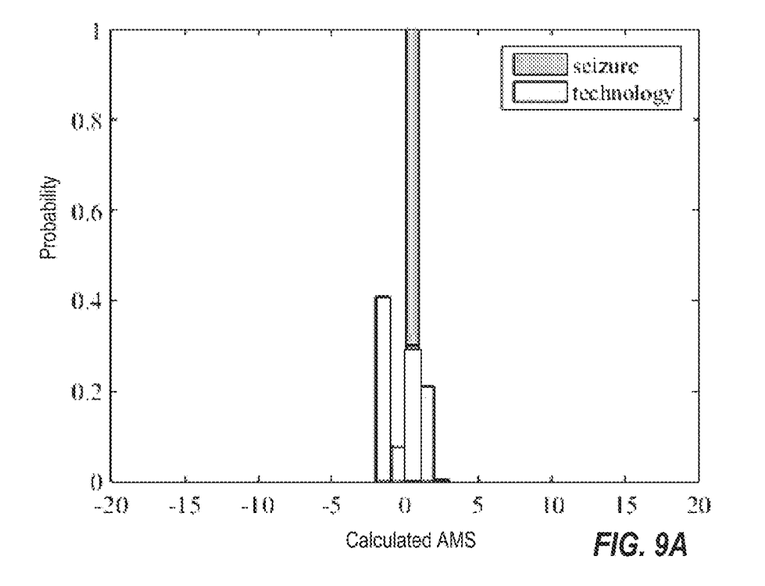
FIG. 9A illustrates one exemplary histogram of calculated AMS versus the probability density function using a single-modal, extra-cerebral sensor for twelve epochs of seizure data and two-hundred randomized epochs of data from a patient using technology (phone, computer).
Figure 9B:
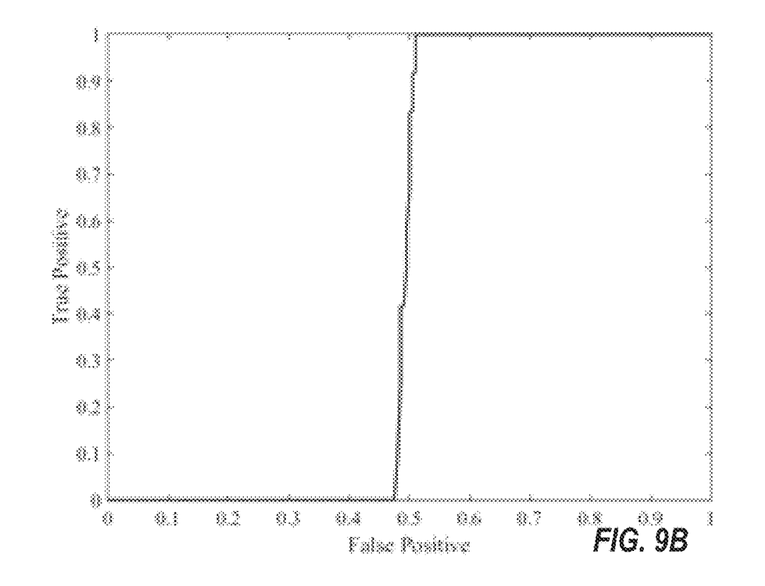
FIG. 9B illustrates the ROC curve for seizure versus technology use in the case of FIG. 9A.

While commercial devices exist for monitoring physiological stress, these are based on single mode data. For example, the Empatica Embrace stems from study of electrodermal response during seizures. In our pilot study, the EDA or GSR transducer contributes seven of the 34 features extracted. In contrast to the AMS analysis for the 34-element feature vector from multi-modal sensing from a plurality of sensors shown in FIG. 7-8, the ROC applied to classification using features derived only from one sensor type such as EDA or GSR sensor data) decreases to 0.51, or just above chance (FIG. 9A-B). The study shows that there is ample sensitivity in multi-modal data acquired with a plurality of non-electroencephalographic sensors to distinguish between ictal and non-ictal states, but single mode sensor data lacks specificity.

Approaches to selecting features from multi-model time-series data involve optimization, windowing, and heuristic or rule-based feature selection. It is clear that single-modality sensors may capture some manifestations of seizures, but they cannot capture all manifestations. For example, tri-axial accelerometers 122 capture motion, but not physiological changes and vocalizations. Electrodermal sensors 130 and ECG sensors 124 capture autonomic system response, but signals may overlap with other behaviors that stimulate similar response (i.e., sweating occurs both during a seizure and during normal exercise). Further, different sensors must be sampled on different time scales to capture signals of interest.

Studies have been made of hybrid discriminative/generative classifiers for modeling of general human activities—sitting, walking, jogging, riding a bicycle—from accelerometers, audio, infrared, temperature, and barometric pressure sensors and derives "boosted decision stumps" as static classifiers for each activity. The method ranks individual features in relation to its ability to discriminate a given action, and the final output is a weighted sum of a set of weak classifiers. While the algorithm is effective in classifying common human activities (sitting, standing, walking, jogging, walking up/down stairs, driving, cycling, riding an elevator), for those activities, single modalities can be effective at identifying the activity. For example, barometric pressure is strongly correlated with elevation change, and accelerometers are strongly correlated with human initiated motion; however, the characteristics of seizures described herein indicate that no single sensor modality captures all manifestations of seizures. The "overlap" in dynamic range from single modalities among ictal and non-ictal states is potentially too large to use iteratively such trained binary weak classifiers based on a single feature or single sensor.

Rather, the dynamic evolution of physiological measures in concert allow us to detect seizures.

Owing to this, system 100 implements a classification system in which simple discriminative or generative classifiers are based on feature vectors that incorporate combinations of elements from each sensor modality, including features derived from spectral properties, i.e., frequency-domain data, and/or wavelet decomposition. Our reasoning is as follows. In seizure manifestations, motion has periodic elements reflecting its repetitive nature. Similarly, vocalizations tend to be repetitive and narrowband rather than broadband. These manifestations may be accompanied by sudden physiological changes, e.g., change in heart rate or respiration rate. During petit mal seizures, the patient experiences a quiet, trance-like state, i.e., the power spectral density of sensors should decrease dramatically and suddenly. In contrast, normal activity is characterized by aperiodic motion (e.g., reading, sitting, housework) or periodic motion of a different frequency (walking, running), which can occur in conjunction with change in heart rate, respiration rate, and electrodermal response. Combinations of features, including frequency-domain features, enables separation of seizure events from normal activity using simple binary discriminative and generative classifiers with sufficient accuracy to generate a query to resolve uncertainty in the class label. Given the query response, a trained classifier that incorporates that response is used to provide a final class label. Combinations of existing sensors and features enable good separation of seizure events from normal activity using simple classifiers with sufficient accuracy to generate a query to resolve uncertainty in the class label.

There are other manifestations of seizures that are not captured explicitly by the transducer set used in FIGS. 7, 8 and 9; for example, facial spasms are characteristic of simple partial seizures and tonic-clonic seizures and can progress in characteristic frequency of the spasms as the seizure progresses. Lateralized, sustained head/eye deviation is common in generalized tonic-clonic seizures, as are other automatisms (grimacing, high frequency facial muscle twitching, lip smacking, chewing, and swallowing, and less commonly, ictal yawning), but EMG on the face that can detect idiosyncratic responses during seizures requires application of differential skin electrodes and thus is obtrusive on the face. Likewise, eye motion is difficult to follow except through use of a camera. Therefore, exemplary embodiments of system 100 include optical sensors (e.g., 134) for eye tracking and facial motion tracking.

In order to tune a classifier (e.g., classifiers 153) to an individual, system 100 incorporates active learning (e.g., learning algorithm 154)—an approach that improves classification through generation of alternative training sets and online training of a classifier using these alternative training sets. An initial classifier embodied on a device is based on training data acquired in the clinic, as described above. When validator 156 queries the patient based on the output of a classifier to confirm an ictal state, the associated data are then labeled as a non-ictal state (if the patient responds as such) or as an ictal state if either the patient does not respond or responds affirmatively. Active learning adds this labeled data to the training set and retrains one or more of classifiers 153 given the additional data. Classifier 153 (and state recognizer 152) thus becomes more accurate for each patient over time—a highly valuable characteristic for wearable medical devices. Further, as false and true positive data are recorded for each event, these data may be mined, being uploaded to a central database, where it may be used to expand a training database used to establish more accurate initial parameters for classifier 153 for use with new patients.

In one embodiment of active learning from structured, unlabeled data, structure imposes constraints on acceptable patterns or evolution of the sensor data; patient-labeled data provide examples of both positive (ictal) states, while data temporally far from the seizure event provide negative examples. A P-expert identifies only false negatives and an N-expert identifies false positives, and each expert is subject to making classification errors. A small number of patient-labeled examples together with a larger number of structured, unlabeled examples updates a classifier as follows: (1) train an initial classifier using labeled data; (2) label unlabeled data with the classifier; (3) identify labels that contradict constraints; (4) correct those labels and add them to the training set; (5) retrain the classifier given new labeled data. In seizure detection, the initial classifier is trained from the clinical data set, and structure is provided by labels acquired through interaction with the patient. Those labels confirm or contradict the label provided by the initial classifier, and the initial classifier is then retrained given new labeled data.

In summary, system 100:
(1) is a seizure monitoring device providing an associated dataset;
(2) embodies an ensemble of generative and discriminative machine learning classifiers to detect and classify seizures from feature vectors derived from a plurality of non-electroencephalographic sensors;
(4) incorporates active learning to improve classification over time based on patient queries; and
(5) is a monitoring device adapted to be worn on the body.

Impacts

System 100 provides benefits to epilepsy patients, their caregivers and clinicians. Most directly, procedures to treat refractory epilepsy can be improved, as system 100 provides accurate count of seizures that occur outside of the clinical environment to clinicians allowing them to select medications and dosages that reduce seizure severity and rates while improving quality of life by minimizing side effects of medications. System 100 also enables a simpler process to change medication regimens, by providing accurate monitoring of seizures outside of the clinical environment, lowering the costs and difficulties to the patient and allowing for more rapid iteration through attempted treatment regimens.

Automated seizure detection provided by system 100 allows accurate recording of the time, duration, and measurement of the severity of seizures for patients with post-ictal amnesia, providing more accuracy than seizure diaries. System 100 provides neurologists a broad and accurate record of seizures that occur in their patients during a normal day, leading to efficient tailoring of therapeutic regimens to optimize both treatment efficacy and tolerability.

A major concern for epilepsy patients is the consequence of having seizures in the absence of a caregiver—essentially everywhere outside home or clinic. The world is a dangerous place if you have no motor control and no awareness of your surroundings. Bystanders unfamiliar with epileptic seizures may not realize that the patient needs short-term protection from harm and possibly medical attention; this device could provide that information. System 100 also increases the confidence of epilepsy patients (e.g., patient 202) and their caregivers by continuous updating of the state of the patient and notifying caregivers of seizures. Ultimately, system 100 improves the quality of life of both parties.

In an embodiment, the system has a speaker driver and loudspeaker in at least one module; in this embodiment, the processor is configured to use the speaker driver and loudspeaker to announce that the patient is having a seizure and should be protected from harm. In an alternative embodiment, in addition to announcing that the patient is having a seizure, the processor is configured to send a text message or email to a medical care provider to report the seizure event.

System 100 may potentially protect patients from, and improve the understanding of mechanisms leading to, status epilepticus (SE) and sudden unexplained death in epilepsy (SUDEP). SE is the most severe form of epilepsy with extended seizures and a mortality rate of up to 20%. It is treated as a medical emergency for seizures lasting longer than five minutes. By reducing emergency response times, system 100 greatly improve SE recovery prognosis. SUDEP is rarely observed in the clinical setting. Thus, the neuropathological mechanisms and environmental factors contributing to fatal seizures are largely unknown. By vastly increasing the observation window and the available dataset of seizure manifestations, system 100, operating as a wearable seizure monitor and recorder, provides key insight into this epilepsy end-state.

Finally, system 100 may also be used to monitor patients who have no prior history of seizures, but have suffered from a traumatic brain injury. A population study of seizure events following traumatic brain injury (TBI) shows that the five-year cumulative probability of seizure events (extracted from medical records) post-TBI ranged from 0.7% in patients with mild TBI to 10% in severe TBI cases. As all data are from self-reported or observed seizure events, it is possible that many seizures within this population go unreported.

Beyond epilepsy, there may be far reaching implications to real-time continuous monitoring of the vital signs collected by system 100. Patients who suffer from other neurological disorders, heart disease, hypertension, obesity, or other chronic diseases may benefit from having vital statistics data collected and correlated to the riskier episodic periods of their condition. With additional development, system 100 may accurately classify accidental falls and thereby improve trauma-response times for at-risk elderly and infirmed patients.

Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as all statements of the scope of the present method and system, which, as a matter of language, might be said to fall therebetween.

What is claimed is:

1. A system for identifying ictal states in a patient, comprising:
    a sensor group consisting of a plurality of non-electroencephalographic sensors selected from the group consisting of photoplethysmographic (PPG) sensors, one or more single or tri-axial accelerometers, electrocardiogram (ECG) sensors, electromyography (EMG) sensors, microphones, temperature sensors, eye-motion sensors, facial movement sensors, galvanic skin response (GSR) sensors, and limb acceleration sensors:
    the plurality of non-electroencephalographic sensors being configured to sense a plurality of non-electroencephalographic signals from the patient;
    a signal processing unit coupled to receive time-series data from a sensor group consisting of only the plurality of non-electroencephalographic sensors and comprising:
    a processor; an output device; and an input device;
    a memory storing machine-readable instructions that when executed by the processor are capable of:
    classifying, using a classifier based upon a training set and implemented by the machine readable instructions, the time-series data from the sensor group to determine a probability of the patient being in an ictal state; and when the probability is greater than a threshold:
    asking the patient if the patient is in an ictal state using the output device;
    if the patient fails to respond to the asking using the input device or enters a positive reply, logging occurrence of a seizure; and
    updating the classifier based upon the time-series data from the sensor group, the probability, and the patient response.

2. The system of claim 1, wherein the classifier implements ensembles of two or more classifiers selected from the group consisting of discriminative classifiers and generative classifiers.

3. The system of claim 1, the memory further comprising machine readable instructions that when executed by the processor are capable of updating at least one of the discriminative classifiers and the generative classifiers based upon the time-series data from the sensor group, the probability, and the patient response.

4. The system of claim 3, the sensor group comprising an ECG sensor and an accelerometer.

5. The system of claim 4, the non-electroencephalographic sensors comprising a sensor selected from the group consisting of a photoplethysmographic (PPG) sensor, a GSR sensor, a microphone, a temperature sensor, a facial movement sensor, and an eye-motion sensor.

6. The system of claim 5 wherein at least one sensor of the sensor group is coupled to the signal processing unit through a short range digital radio.

7. The system of claim 4, wherein the classifier incorporates machine readable code for machine learning to improve reliability of identifying the ictal state for the patient over time.

8. The system of claim 1, wherein the signal processing unit comprises a smartphone.

9. The system of claim 1 wherein the processor generates a report to a caregiver that the patient is in the ictal state if one of a positive reply and no reply is received in response to the asking.

10. The system of claim 1, the memory further comprising machine readable instructions that when executed by the processor are capable of processing the time-series data from the sensor group to determine at least one feature vector.

* * * * *

UNITED STATES PATENT AND TRADEMARK OFFICE
CERTIFICATE OF CORRECTION

| | | |
|---|---|---|
| PATENT NO. | : 10,485,471 B2 | Page 1 of 1 |
| APPLICATION NO. | : 15/400789 | |
| DATED | : November 26, 2019 | |
| INVENTOR(S) | : Laura Ray et al. | |

It is certified that error appears in the above-identified patent and that said Letters Patent is hereby corrected as shown below:

In the Specification

Column 1, Lines 13-16 should read as follows:
--This invention was made with government support under NSF Grant No. 1112753 awarded by the National Science Foundation, and Grant No. W81XWH-18-1-0712 awarded by the Defense Health Agency, Medical Research and Development Branch. The government has certain rights in the invention.--

Signed and Sealed this
Fifteenth Day of October, 2024

Katherine Kelly Vidal
*Director of the United States Patent and Trademark Office*